United States Patent [19]

Chand

[11] 4,399,942

[45] Aug. 23, 1983

[54] GAS EMITTING DEVICE

[75] Inventor: Ramesh Chand, Woodland Hills, Calif.

[73] Assignee: GC Industries, Chatsworth, Calif.

[21] Appl. No.: 319,462

[22] Filed: Nov. 9, 1981

[51] Int. Cl.³ ............................................. B05B 17/00
[52] U.S. Cl. ....................................................... 239/34
[58] Field of Search ........................... 239/34; 422/101; 261/99, 104; 73/864.81

[56] References Cited

U.S. PATENT DOCUMENTS 3,788,545  1/1974  Budd et al. ............................ 239/34
3,856,204  12/1974  Chand .................................... 239/34

Primary Examiner—Andres Kashnikow
Attorney, Agent, or Firm—Fulwider, Patton, Rieber, Lee & Utecht

[57] ABSTRACT

A device for emitting a gas at a constant rate into a moving fluid medium to produce an accurately known concentration of the gas in the medium. The gas is held in a cylinder (10) in which there are two chambers (14 and 16), one for holding the substance in liquefied form and the other for holding it solely in gaseous form. The substance permeates through a permeable material (20) between the two chambers and then through another quantity of permeable material (12) positioned at an exit from the second chamber (16). The device combines low temperature sensitivity associated with gaseous phase devices, and high permeation rates and lone useful lives associated with liquid phase devices. It is also safer than prior devices of the same general type.

16 Claims, 3 Drawing Figures

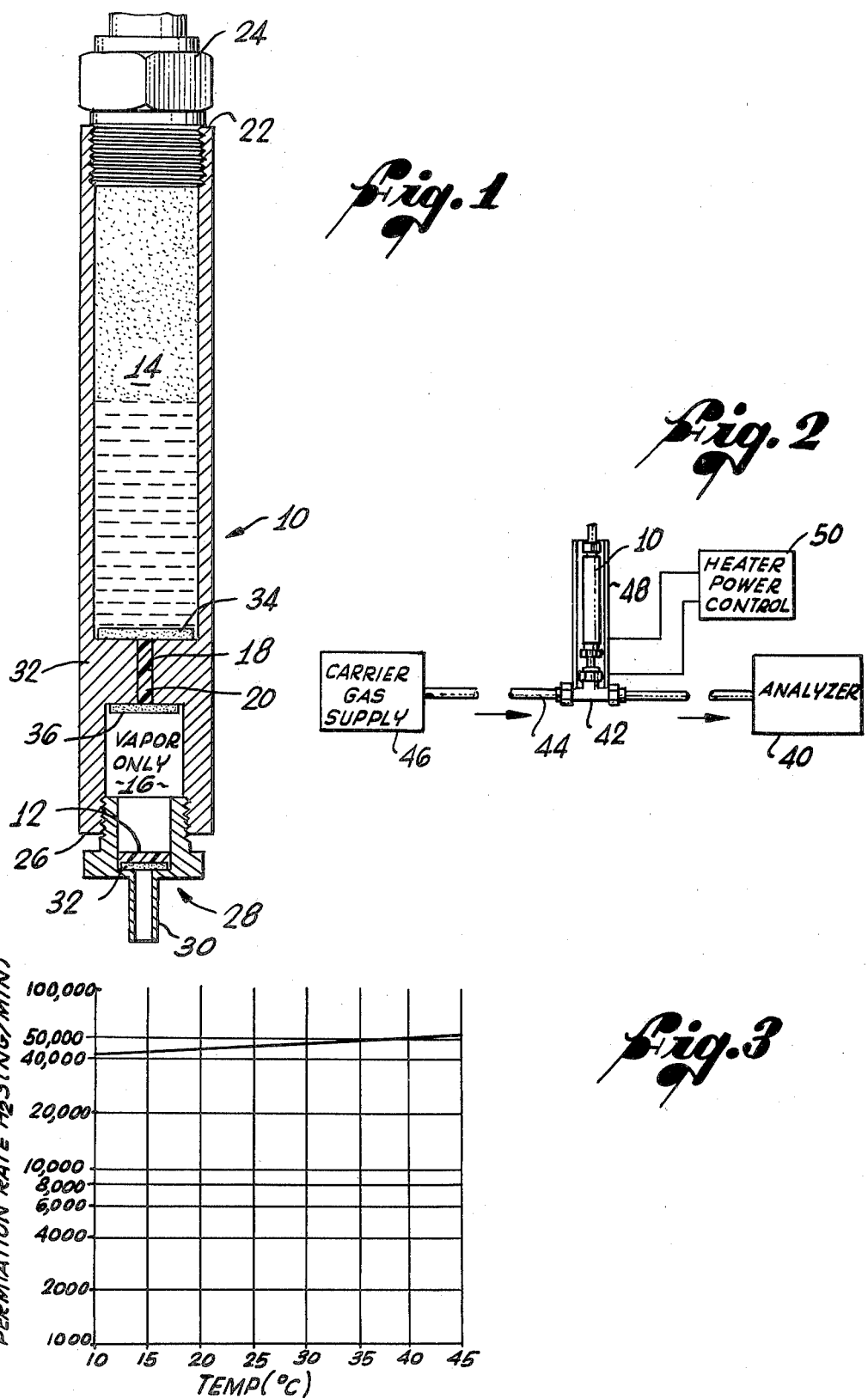

GAS EMITTING DEVICE

BACKGROUND OF THE INVENTION

This invention relates generally to devices for the emission of a gas at a constant rate, and, more particularly, to such gas emitting devices used in the production of calibration samples for gas or liquid analyzers. Gas is emitted from such a device through a permeable material, and mixed with a moving fluid medium for use in an analyzer.

This inventor's prior patent, U.S. Pat. No. 3,856,204, represented a significant advance in the field of gas emitting devices. Prior to the invention described and claimed in the patent, gas emitting devices had employed an elongated tube of a permeable, polymeric plastic material to hold the gas under pressure and partially in the liquid phase. At a constant temperature, the vapor pressure of the substance is also constant, and molecules of the substance permeate through the walls of the tube at a constant rate, thereafter to be intermixed or dissolved in a moving fluid medium stream surrounding the tube. However, as discussed in the aforementioned patent, tube devices of this type suffered from major disadvantages. In the invention disclosed in the prior patent, the substance to be emitted is held in a sealed vessel having a passage filled with a permeable polymeric plastic material, through which the substance can permeate and be emitted outside the vessel. The permeable material used in the device provides for use of a much higher permeation rate, and the device has a much lower sensitivity to temperature variations, is comparison with the prior devices.

Although the device disclosed in the inventor's prior patent represented a significant advance in the field, the device still falls short of perfection in some areas of application. Although the device has relatively low sensitivity to temperature variations, it is nevertheless more sensitive to temperature variations when the substance to be emitted is stored in the liquid phase. When the substance is stored in the gaseous phase, an extremely favorable temperature characteristic is obtained. However, much smaller quantities of the substance can be held in the gaseous phase than in the liquid phase. When relatively high permeation rates are required, such as 20,000 to 50,000 nanograms (ng) per minute or higher, an impractically large gaseous phase permeation device is needed, or its useful life is extremely limited. Liquid phase devices, on the other hand, permit the use of relatively high permeation rates and long useful lives, but suffer from the significant drawback of a relatively poor temperature characteristic. Another difficulty with liquid phase devices is that the liquid substance is sometimes detrimental to the permeable material, greatly reducing the life of the device. Furthermore, the permeable material can be dislodged from the passage and the substance stored under pressure can be released in an explosive and sometimes dangerous manner.

It will be apparent from the foregoing that there is still a significant need for improvement in gas emitting devices of this type. What is particularly needed is a device retaining the advantages of the one disclosed in the inventor's prior patent, but avoiding its inherent disadvantages. The present invention fulfills this need.

SUMMARY OF THE INVENTION

The present invention resides in a gas emitting device having the principal advantage of a gaseous phase permeation device, i.e., relatively low sensitivity to temperature variation, and having the principal advantage of a liquid phase device, i.e., the capability to provide high permeation rates over relatively long useful lives, while still using a small volume for storage. Briefly, and in general terms, the device of the invention comprises a first chamber in which the substance to be emitted is stored under pressure at least partially in the liquid phase, a second storage chamber in which the substance to be emitted is stored only in the vapor or gas phase, fluid communication means connecting the first and second chambers and enclosing a quantity of permeable material through which the substance permeates from the first chamber to the second chamber, an exit from the second chamber, and, positioned at the exit, another quantity of permeable material through which the substance in the second chamber permeates at a predetermined rate. Gas permeation from the second chamber may be at a relatively high permeation rate, and may be sustained for a long period of time because of the continued permeation of the substance from the first chamber to the second chamber.

Since the liquid-phase substance is stored only in the first chamber, and the choice of permeable material in the fluid communication means does not determine the rate of gas permeation from the device, this permeable material may be one selected to be resistant to damage from highly corrosive liquids, such as liquified sulfur dioxide ($SO_2$). The other quantity of permeable material is selected solely for its permeability and temperature characteristics, and is practically undamaged by the same substance in the gaseous phase.

More specifically, the first and second chambers in a presently preferred embodiment of the invention are defined by a unitary tubular structure, with the first chamber and second chamber located at opposite end portions of the structure. Separating the two chambers is a common wall, and the fluid communication means between the chambers is defined by an axial passage through the wall, the first-mentioned quantity of permeable material being positioned in the passage. A removable plug seals the substance in the first chamber, and an adaptor assembly forms a closure for the second chamber and provides the exit at which the other quantity of permeable material is located. In the preferred embodiment of the device, porous filters are provided at both ends of the passage between the two chambers, and at the exit from the second chamber. The filters provide little resistance to the flow of gas, but function both to remove contamination from the gas stream and also to minimize the risk of dangerous sudden release of the material under pressure.

It will be appreciated from the foregoing that the present invention represents a significant advance in the field of gas emitting devices. In particular, the invention provides a permeation device with the favorable temperature characteristics of a gaseous or phase device, but with the high permeation rate and long life of a liquid phase device. Moreover, by proper selection of the permeable materials, damage due to contact with stored liquid substances can be minimized or practically eliminated. Other aspects and advantages of the invention will become apparent from the following more detailed description, taken in conjunction with the accompanying drawings.

BRIEF DESCRIPTION OF THE DRAWINGS

FIG. 1 is a cross-sectional view of a device embodying novel aspects of the present invention;

FIG. 2 is a partly schematic view illustrating how the device of FIG. 1 is connected to an analyzer; and FIG. 3 is a graph illustrating the temperature characteristic of the device.

DESCRIPTION OF THE PREFERRED EMBODIMENT

As shown in the drawings for purposes of illustration, the device of the present invention is used to dispense a gaseous substance at a constant rate, the gas thereafter being mixed with a moving fluid medium to provide a sample containing a known concentration of the gas, which is then typically used to calibrate an analyzer of gases or liquids. The device includes a sealed vessel, indicated generally by reference numeral 10, in which a substance to be emitted is stored under pressure, and a quantity of permeable material 12 through which the stored substance permeates at a predetermined rate.

In accordance with the invention, the vessel 10 includes two separate storage chambers 14 and 16 connected by a passage 18 in which another quantity of permeable material 20 is positioned. The substance is stored in the first chamber 14 under sufficient pressure to maintain the substance partly in the liquid phase, in equilibrium with the remainder of the substance in the gaseous phase. Permeation through the passage 18 continues at a rate determined by the pressure in the second chamber 16, which is, in turn, determined by the rate of gas emission from the second chamber. In any event, the substance held in the second chamber 16 is in the gaseous phase only. Consequently, the permeation characteristics of the entire device are those of a gaseous phase emitter, but the relatively large storage capability in the liquid phase chamber 14 allows for the use of high permeation rates from the device over relatively long operating periods.

More specifically, the vessel 10 employed in the presently preferred embodiment of the invention is a hollow cylinder of stainless steel or other material impervious to, and practically nonreactive with the substance to be contained therein. The cylinder 10 has an open upper end 22 threaded internally to receive a plug or pressure seal 24, which is normally not removed except for refilling the cylinder. The cylinder 10 also has an open lower end 26 internally threaded to receive an exit adapter assembly 28 having a reduced-diameter exit nipple 30. The first quantity of permeable material 12 is lodged together with a porous filter 31, in the assembly 28 and in the flow of gas into the exit nipple 30. The chambers 14 and 16 are defined in part by the walls of the cylinder 10 and in part by a relatively thick, common integral wall 32 separating the two chambers. The wall 32 separates the chambers 14 and 16 completely except for the passage 18, which is axially oriented in the center of the cylinder 10. Two additional porous filters 34 and 36 are positioned at the ends of the axial passage 18.

As in the device shown in the present inventor's prior U.S. Pat. No. 3,856,204, the permeable material 12 through which gas is emitted from the device is preferably a silicone polymeric compound chemically classified as a dimethyl polysiloxane. Many compounds of this type are commercially available and can be used in the present invention. By way of example, dimethyl compound PR1939, manufactured by Products Research and Chemical Corp., Los Angeles, Calif., and dimethyl RTV compound 630, manufactured by General Electric Co., Waterford, New York, have each been found suitable in the presently preferred embodiment.

The silicone material 12 is cured at a temperature of approximately 120° F., preferably for at least 24 hours. During curing, the silicone material hardens and becomes permanently bonded to the walls of the adapter assembly 28. Various adapter assemblies may be readily substituted at the lower end 26 of the vessel 10, to provide a selection of permeation rates.

The permeable material 20 in the passage 18 may also be a silicone polymeric compound of the same type as the material 12. However, it may be desirable in some cases to use a different permeable material providing resistance to corrosion or dissolution by the liquid phase of the substance in the first chamber 14. Since the rate at which gas is emitted from the device is not dependent on the selection of the material 20, which need only be at least as permeable as material 18, the material 20 can be selected for its corrosion resistance. For example, if an appropriate polyfluorocarbon material is used, highly corrosive liquified gases such as nitrogen dioxide ($NO_2$) or sulfur dioxide ($SO_2$) can be stored in the chamber 14 without damage to the permeable material 20. The gaseous form of these substances in the second chamber 16 has no significant corrosive effect on the silicone material 12. Examples of suitable polyfluorocarbons are Teflon (polytetrafluoroethylene) and Viton (copolymers of vinylidene fluorides and hexafluoropropylene), both trademarks of E.I. du Pont de Nemours & Co., Inc.

The permeable material 20 is also cured in position after appropriately cleaning the entire vessel 10 and applying a vacuum to draw in the permeable material 20 and remove all air bubbles from the passage. The filters 31, 34 and 36, are, in the presently preferred embodiment of the invention, formed from powdered stainless steel particles of 10–100 micron size, sintered to form disk-shaped elements.

FIG. 2 illustrates diagrammatically how the device of the present invention would typically be connected for use. For calibrating an analyzer 40, the cylinder 10 is connected by a T-junction 42 to emit the gaseous substance at a constant rate into a fluid medium flowing at a constant rate along a pipe 44 into the analyzer. The fluid medium may be an inert gas, such as nitrogen, in which the emitted substance is mixed, or, in some applications, it may be a liquid in which the emitted substance is dissolved. The fluid medium is drawn from a supply system 46, which typically includes a pump, a pressure regulator and a flow meter, none of which are illustrated. A constant temperature is preferably maintained by means of some type of heating element 48 wrapped around the cylinder 10 and supplied with power through a control unit 50, which includes an adjustable thermostat (not illustrated), thus maintaining a constant rate of emission of the substance contained in cylinder 10.

In some cases, temperature control may not be necessary, since the device has an extremely flat permeation-temperature characteristic. This is illustrated in FIG. 3, which, by way of example, shows the variation of the permeation rate of hydrogen sulfide ($H_2S$) over a temperature range from 10° to 45° C. It will be apparent that permeation rates as high as 50,000 ng per minute, or even higher, are possible with practically little change in the permeation rate with temperature. Moreover, this performance can be achieved using a device of relatively small size, e.g., approximately 1.0 inch (2.54 cm) in diameter and approximately 7.0 inches (17.8 cm) long. Prior to the invention, a typical gaseous phase permeation device had a diameter of 2-3 inches (5-7 cm) and a length of 8-9 inches (20 cm), and was still limited to a permeation rate of only approximately 1,000 ng per minute.

Another significant benefit arising from use of the invention is that the device is extremely safe compared with one using only a single quantity of polymeric permeable material. Since the device of the invention includes two quantities of polymeric permeable material and a total of three porous filters positioned between the exit of the device and the high pressure storage chamber 14, the likelihood of inadvertent release of the substance stored under high pressure is extremely low. For example, even hydrogen sulfide, which is stored at a gauge pressure of over 250 pounds per square inch (17,577 $gm/cm^2$), can be safely stored and emitted from the device as described.

It will be appreciated from the foregoing that the present invention represents a significant advance in the field of gas emitting devices. In particular, it provides a gas emitter not only with the desirable temperature characteristic of a gaseous phase device, but also with the desirable high permeation rate and long useful life of a liquid phase device. In addition, the device is safer to use and is less susceptible to corrosion by the liquified substances from which the gases are dispensed. It will also be appreciated that, although a specific embodiment of the invention has been described in detail for purposes of illustration, various modifications may be made without departing from the spirit and scope of the invention. Accordingly, the invention is not to be limited except as by the appended claims.

I claim:

1. A gas emitting device, comprising:
   a first chamber, in which a substance to be emitted is stored at least in part in the liquid phase;
   a second chamber, in which the substance to be emitted is stored solely in the gaseous phase, said second chamber having an exit;
   fluid communication means connecting said first and second chambers;
   a first quantity of permeable material located at said exit to provide a preselected rate of permeation of gas from said device; and
   a second quantity of permeable material positioned in said fluid communication means, to permit permeation of gas, but not liquid, into said second chamber;
   whereby the emission rate from said device is relatively insensitive to temperature variations, but may be maintained at high levels over long periods of operation because of the high storage capacity of said first chamber.

2. A gas emitting device as set forth in claim 1, wherein:
   said second quantity of permeable material is selected to be resistant to damage from the liquefied form of the substance in said first chamber.

3. A gas emitting device as set forth in claim 2, wherein:
   said first quantity of permeable material is a dimethyl polysiloxane; and
   said second quantity of permeable material is a polyfluorocarbon.

4. A gas emitting device as set forth in claim 1, and further including:
   a plurality of filter elements disposed adjacent to said first and second quantities of permeable material, to remove impurities from the substance to be emitted, and to reduce the risk of explosive release of the substance.

5. A gas emitting device as set forth in claim 1, which:
   said first and second chambers are defined by a unitary tubular structure having an integral wall common to both said chambers; and
   said fluid communication means includes an axial passage through said integral wall.

6. A gas emitting device as set forth in claim 5, wherein:
   said second quantity of permeable material is located in said passage;
   said exit is provided by an adaptor assembly removably affixed to said tubular structure.

7. A gas emitting device as set forth in claim 6, and further including:
   a first porous filter also located at said exit, adjacent to said first quantity of permeable material; and
   at least one additional porous filter, located at at least one end of said axial passage.

8. A gas emitting device as set forth in claim 7, wherein said porous filters are of stainless steel material.

9. A gas emitting device comprising:
   a tubular vessel for storage of a substance to be emitted as a gas, said tubular vessel having an integral wall between its ends, dividing said vessel into first and second chambers;
   means for sealing said first chamber after introduction, in liquefied form, of the substance to be emitted;
   means defining an exit from said second chamber;
   an axial passage through said integral wall;
   a first quantity of permeable material located in said passage to provide for permeation of the substance into said second chamber, for intermediate storage in gaseous form; and
   a second quantity of permeable material located in said passage to provide for permeation of the substance into said second chamber, for intermediate storage in gaseous form;
   whereby the emission rate from said device is relatively insensitive to temperature variations, but may be maintained at high levels over long periods of operation because of the high storage capacity of said first chamber.

10. A gas emitting device as set forth in claim 9, wherein:
    said means defining an exit includes a removable exit assembly, to provide one of a selection of permeation rates by replacing said assembly.

11. A gas emitting device as set forth in claim 8, wherein:
    said second quantity of permeable material is selected to be resistant to damage from the liquefied form of the substance in said first chamer.

12. A gas emitting device as set forth in claim 11, wherein:
    said first quantity of permeable material is a dimethyl polysiloxane; and said second quantity of permeable material is a polyfluorocarbon.

13. A gas emitting device as set forth in claim 8, and further including:
   a first porous filter also located at said exit, adjacent to said first quantity of permeable material; and
   at least one additional porous filter, located at at least one end of said axial passage.

14. A gas emitting device, comprising:
   a tubular vessel having an integral internal wall intermediate its ends, said wall dividing said vessel into first and second chambers;
   a threaded removable seal for sealing said first chamber after the introduction, in liquefied form, of a substance to be emitted as a gas from the device;
   a threaded exit assembly forming a closure for said second chamber, and having an exit passage;
   a first quantity of permeable material positioned at said exit passage to provide emission of the substance at a predetermined rate;
   an axial passage through said integral wall between said first and second chambers;
   a second quantity of permeable material positioned in said axial passage, to allow for permeation of the substance from said first chamber to said second chamber, to replenish the supply of gaseous substance for emission;
   a first porous filter located at said exit passage, adjacent said first quantity of permeable material; and
   second and third porous filters located at the ends of said axial passage;
   whereby the emission rate from said device is relatively insensitive to temperature variations, but may be maintained at high levels over long periods of operation because of the high voltage capacity of said first chamber.

15. A gas emitting device as set forth in claim 14, wherein:
   said second quantity of permeable material is selected to be resistant to damage from the liquefied form of the substance in said first chamber.

16. A gas emitting device as set forth in claim 15, wherein:
   said first quantity of permeable material is a dimethyl polysiloxane; and
   said second quantity of permeable material is a polyfluorocarbon.

* * * * *